United States Patent [19]

Mori et al.

[11] Patent Number: 4,877,441
[45] Date of Patent: Oct. 31, 1989

[54] FUNGICIDAL SUBSTITUTED CARBOXYLIC ACID DERIVATIVES

[75] Inventors: Tatsuya Mori; Tadashi Ohsumi; Shigeo Nakamura; Kiyoto Maeda; Sumio Nishida; Hirotaka Takano, all of Hyogo, Japan

[73] Assignee: Sumitomo Chemical Company Ltd., Osaka, Japan

[21] Appl. No.: 259,283

[22] Filed: Oct. 18, 1988

[30] Foreign Application Priority Data

| Nov. 6, 1987 | [JP] | Japan | 62-281563 |
| Nov. 6, 1987 | [JP] | Japan | 62-281564 |
| Nov. 6, 1987 | [JP] | Japan | 62-281565 |
| Jul. 15, 1988 | [JP] | Japan | 63-177751 |
| Jul. 29, 1988 | [JP] | Japan | 63-191919 |
| Jul. 29, 1988 | [JP] | Japan | 63-191920 |
| Aug. 2, 1988 | [JP] | Japan | 63-193598 |

[51] Int. Cl.$^4$ .................. C07D 417/12; C07D 405/12; A01N 43/78; A01N 43/56
[52] U.S. Cl. .................................. 71/90; 71/88; 71/92; 71/94; 548/194; 548/200; 548/374; 549/469
[58] Field of Search ................ 546/269; 548/194, 200, 548/374; 549/469; 71/88, 90, 92, 94

[56] References Cited

U.S. PATENT DOCUMENTS 4,134,987  1/1979  Huppatz .......................... 424/273 P

FOREIGN PATENT DOCUMENTS 2611601A  9/1977  Fed. Rep. of Germany.
60-34949A  6/1985  Japan.

OTHER PUBLICATIONS

Pestic. Sci., 1971, vol. 2, pp. 43–44.
Aust. J. Chem., 1983, 36, 135–147.
Pesticide Biochemistry & Physiology 5, 380–395 (1975).
Pesticide Biochemistry & Physiology 14, 26–40 (1980).
Phytopathology, 60, 1164–1169 (1970).
CA 70, 87999 J.
Chemical Abstracts, vol. 102, No. 7, 1985, p. 571.
Chemical Abstracts, vol. 103, No. 19, 1985, pp. 712–713.

Primary Examiner—Richard A. Schwartz
Assistant Examiner—Richard A. Sharpe
Attorney, Agent, or Firm—Ladas & Parry

[57] ABSTRACT

A substituted carboxylic acid derivative which is fungicidally active is provided. The compound has the formula:

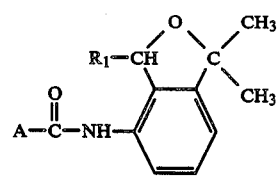

wherein $R_1$ stands for a methyl or ethyl group, A stands for

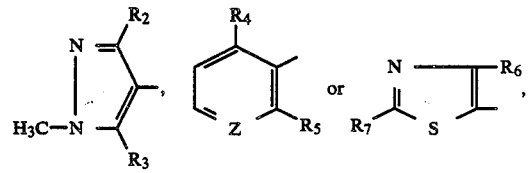

$R_2$ stands for a methyl, ethyl or trifluoromethyl group, $R_3$ stands for a methyl group or a halogen or hydrogen atom, $R_4$ stands for a fluorine or hydrogen atom, $R_5$ stands for a methyl, nitro or trifluoromethyl group or a halogen atom, Z stands for a =CH— group or an N atom, $R_6$ stands for a methyl, ethyl or trifluoromethyl group and $R_7$ stands for an amino or methyl group or a chlorine atom.

12 Claims, No Drawings

FUNGICIDAL SUBSTITUTED CARBOXYLIC ACID DERIVATIVES

The present invention relates to substituted carboxylic acid derivatives, processes for preparing the same and agricultural or horticultural fungicides containing the same as an active ingredient.

Fungicidal activity of some carboxylic acid derivatives is reported in e.g., Japanese patent Kokai Nos. 52-87168, 58-96069 and 60-34949, U.S. Pat. No. 4134987, G. A. Whites: "Pesticide Biochemistry and Physiology" 14, 26 (1980), J. L. Huppatz: Aust. J. Chem. 36, 135 (1983), B. Janks: Pestic. Sci., 2, 43, 1971, DEOS 2611601, Chem. Abst. 70, 87799j (S. African 67 06, 681 Uniroyal Inc.), G. A. White et al.: "Pesticide Biochemistry and Physiology" 5, 380–395, 1975 and M. Shell et al.: Phytopathology 60, 1164–1169, 1970. However, chemicals have been demanded which have higher fungicidal activity, since those known compounds are not satisfactory in activity.

After extensive research on compounds having high fungicidal activity has been made, the present inventors find substituted carboxylic acid derivatives (hereinafter referred to as the present compound) having the formula:

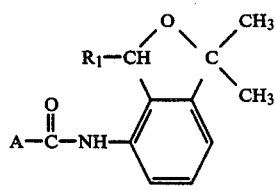

wherein $R_1$ stands for a methyl or ethyl group; A stands for

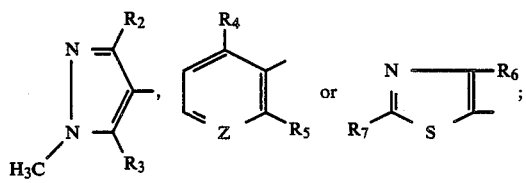

$R_2$ stands for a methyl, ethyl or trifluoromethyl group; $R_3$ stands for a methyl group or a halogen or hydrogen atom; $R_4$ stands for a fluorine or hydrogen atom; $R_5$ stands for a methyl, nitro, or trifluoromethyl group or a halogen atom; Z stands for a =CH— group or an N atom; $R_6$ stands for a methyl, ethyl or trifluoromethyl group; and $R_7$ stands for an amino, methyl group or a chlorine atom.

According to the present invention, processes for preparing the present compound and agricultural or horticultural fungicides containing the present compound as an active ingredient are provided, too.

The present compound has preventive, curative and systemic controlling effects on various plant microbes, especially on plant diseases caused by microbes belonging to Basidiomycetes and gives almost no adverse influence to environment.

The following are plant diseases on which the present compound has an excellent controlling effect; *Rhizoctonia solani* and *Rhizoctonia oryzae, R. solani* III B on rice plant; *Puccinia striiformis, P. graminis, P. recondita, P. hordei, Typhula incarnata, T. ishikariensis, Ustilago tritici* and *U. nuda* on wheat and barley; *Rhizoctonia solani* and *Corticium rolfsii* on various crops; *Rhizoctonia solani* on potato and beet; *Gymnosporangium haraeanum* on pear; *Venturia inaequalis* on apple; *Rhizoctonia solani, Corticium rolfsii, Uromyces trifolii* and *Typhula incarnata, T. ishikariensis* on pasture and lawn.

Preferred compound among the present ones from a view point of fungicidal activity is a substituted carboxylic acid derivative having the formula:

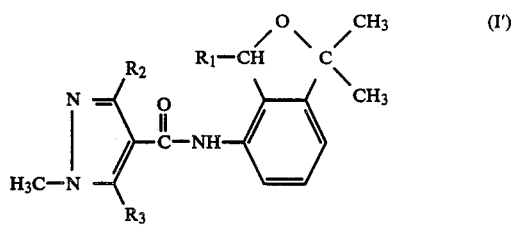

wherein $R_1$, $R_2$ and $R_3$ are the same as those defined above, more preferred is one having the formula:

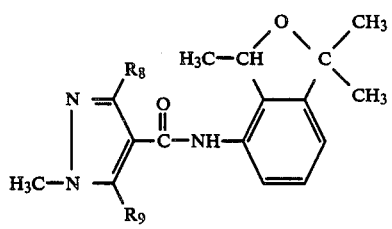

wherein $R_8$ stands for a methyl or trifluoromethyl group and $R_9$ stands for a halogen atom, and the most preferred ones are

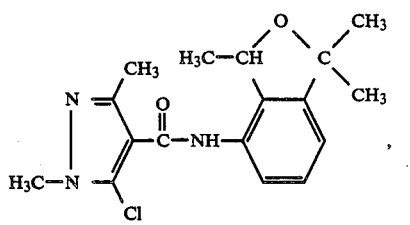

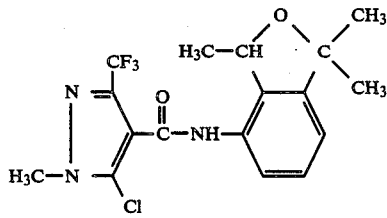

and

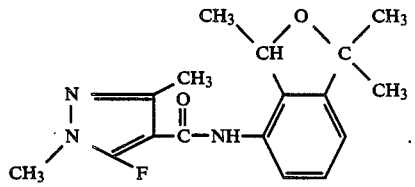

The present compound includes optically active isomers thereof which owe to an asymmetric carbon atom existed therein. One of the isomers is a substituted carboxylic acid derivative having the formula:

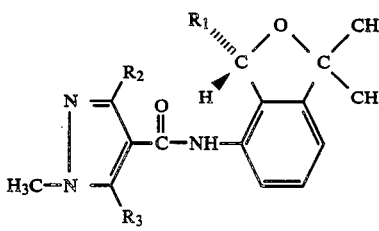 (II)

wherein R₁, R₂ and R₃ have the same meanings as those defined above.

Method for preparing the present compound will be explained in detail below.

Method (A)

Among the present compounds, a substituted carboxylic acid derivative having the formula:

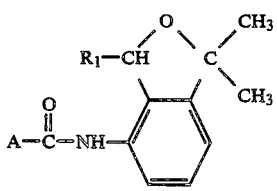 (I)

wherein A and R₁ have the same meanings as those defined above, is prepared by allowing a substituted carboxylic acid having the formula:

 (III)

wherein A has the same meaning as that defined above, or its reactive derivative to react with a substituted 4-amino-2-oxaindan having the formula:

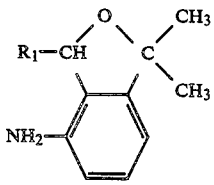 (IV)

wherein R₁ has the same meaning as that defined above.

The reaction is usually conducted in the presence of solvent which is not always necessary. The solvents are, for example, hydrocarbons such as benzene, toluene and xylene, halogenated hydrocarbons such as chlorobenzene, methylene chloride, chloroform and carbon tetrachloride, ethers such as diisopropyl ether, tetrahydrofuran and dioxane, ketones such as acetone and methyl ethyl ketone, esters such as ethyl acetate, nitriles such as acetonitrile, dimethylsulfoxide, dimethylformamide, water, etc., preferably tetrahydrofuran.

Amounts of the reagents used in said reaction are 0.4–1.5 equivalents, preferably 0.5–1.1 equivalents of the substituted carboxylic acid represented by the formula (III) or reactive derivative thereof per equivalent of the substituted 4-amino-2-oxaindan represented by the formula (IV).

The reaction is carried out at optional temperature from the freezing point to the boiling point of the solvent, preferably from 0° C. to the boiling point of the solvent.

The substituted carboxylic acid represented by the formula (III) or reactive derivative thereof includes the corresponding carboxylic acids, acid anhydrides, acid chlorides, acid bromides, carboxylic esters, etc.

The reaction may be conducted in the presence of a reaction assistant depending on the substituted carboxylic acids represented by the formula (III) or reactive derivatives thereof. The reaction assistant is, for example, 1-(3-dimethylaminopropyl)-3-ethylcarbodiimidemethiodide and dicyclohexylcarbodiimide when carboxylic acid is used, sodium hydride, sodium methylate, sodium ethylate, etc. when carboxylic ester is used, and sodium hydroxide, potassium hydroxide, triethylamine, N-methylmorpholine, pyridine etc., when acid halide or acid anhydride is used. The reaction assistant is usually used in an amount of from a catalytic amount to 2 equivalents, preferably 0.95–1.1 equivalents.

After the reaction is over, the reaction assistant or reaction products thereof are removed by filtration or washing with water. The solvent was removed by distillation to give the desired substituted carboxylic acid derivatives of the formula (I). If necessary, the product is further subjected to chromatography, recrystallization, etc. in order to purify the same.

Method (B)

Among the present compounds, a substituted carboxylic acid derivative having the formula (II) is produced by allowing a substituted carboxylic acid having the formula:

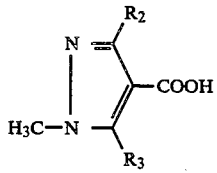 (V)

wherein R₂ and R₃ are the same as those defined above, or a reactive derivative thereof to react with a substituted 4-amino-2-oxaindan having the formula:

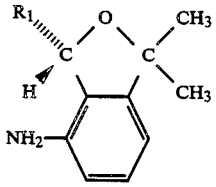 (VI)

wherein R₁ is the same as that defined above.

The reaction is usually conducted in the presence of solvent, which is not always necessary. Examples of the solvent are hydrocarbons such as benzene, toluene and xylene, halogenated hydrocarbons such as chlorobenzene, methylene chloride, chloroform and carbon tetrachloride, ethers such as diisopropyl ether, tetrahydrofuran and dioxane, ketones such as acetone and methyl ethyl ketone, esters such as ethyl acetate, nitriles such as acetonitrile, dimethylsulfoxide, dimethylformamide and water, preferably tetrahydrofuran.

Amounts of the reagents are 0.4–1.5 equivalents, preferably 0.5–1.1 equivalents of the substituted carboxylic acid represented by the formula (V) or reactive derivatives thereof per equivalent of the substituted 4-amino-2-oxaindan represented by the formula (VI).

The reaction is conducted at a temperature of from the freezing point to the boiling point of the solvent, preferably from 0° C. to the boiling point of the solvent.

The substituted carboxylic acid having the formula (V) or reactive derivatives thereof are the corresponding carboxylic acids, acid anhydrides, acid chlorides, acid bromides and carboxylic esters.

The reaction may be conducted in the presence of a reaction assistant depending on the substituted carboxylic acids having the formula (V) or reactive derivatives. Reaction assistants are, for example, 1-(3-dimethylaminopropyl)-3-ethylcarbodiimidemethiodide and dicyclohexylcarbodiimide when carboxylic acid is used; sodium hydride, sodium methylate and sodium ethylate when carboxylic ester is used; and sodium hydroxide, potassium hydroxide, triethylamine, N-methylmorpholine and pyridine when acid halide or acid anhydride is used. The reaction assistant is usually used in an amount of from a catalytic amount to 2 equivalents, preferably 0.95–1.1 equivalents.

After the reaction is over, the reaction assistant or reaction products thereof are removed by filtration or washing with water. The solvent was removed by distillation to give the desired substituted carboxylic acid derivatives of the formula (II). If necessary, the product is further subjected to chromatography, recrystallization, etc. in order to purify the same.

Method (C)

Among the present compounds, a substituted carboxylic acid derivative having the formula:

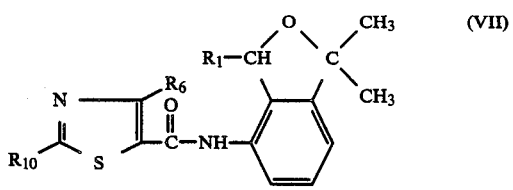  (VII)

wherein $R_1$ and $R_6$ are the same as those defined above and $R_{10}$ stands for an amino or methyl group is prepared by allowing a substituted 4-amino-2-oxaindan derivative having the formula:

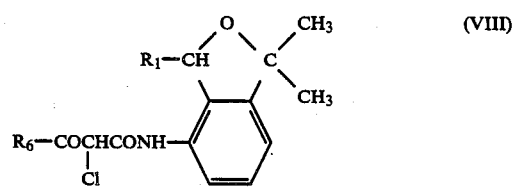  (VIII)

wherein $R_1$ and $R_6$ are the same as those defined above, to react with a thioamide derivative having the formula:

  (IX)

wherein $R_{10}$ is the same as that defined above.

The reaction is usually conducted in the presence of a solvent which is not always necessary. Examples of the solvent are hydrocarbons such as benzene, toluene and xylene, halogenated hydrocarbons such as chlorobenzene, ethers such as diisopropyl ether, tetrahydrofuran and dioxane, esters such as ethyl acetate, alcohols such as methanol and ethanol, dimethylsulfoxide, dimethylformamide and water.

Amounts of the reagents are not critical but usually 0.5–10 equivalents, preferably 1–3 equivalents of the thioamide derivative having the formula (IX) per equivalent of the substituted 4-amino-2-oxaindan derivative having the formula (VIII).

The reaction is conducted at a temperature of from the freezing point of the solvent to the boiling point thereof, preferably from 0° C. to the boiling point of the solvent.

The reaction may be conducted in the presence of a base as a reaction assistant. The base is, for example, ammonia water, amines such as triethylamine and N-methylmorpholine, and inorganic bases such as potassium carbonate and sodium carbonate.

After the reaction is over, the reaction assistant or reaction products thereof are removed by filtration or washing with water, and then the filtrate is subjected to distillation to remove the solvent until the desired substituted carboxylic acid derivative having the formula (VII) is obtained. If necessary, the product may be purified by, for example, chromatography.

Method (D)

Among the present compounds, a substituted carboxylic acid derivative having the formula (II) is also prepared by subjecting a substituted carboxylic acid derivative having the formula (I') to an optically active column, for example, "Sumipack OA"® 4100 (Sumika Chemical Analysis Service Ltd.) until a separation is made.

Substituted 4-amino-2-oxaindan having the formula (IV), one of the starting materials for preparing the present compound, is prepared, for example, from 4-acetaminophthalide mentioned in Jean Vene and Jean Tirouflet Compt rend 231, 911–12 (1950):

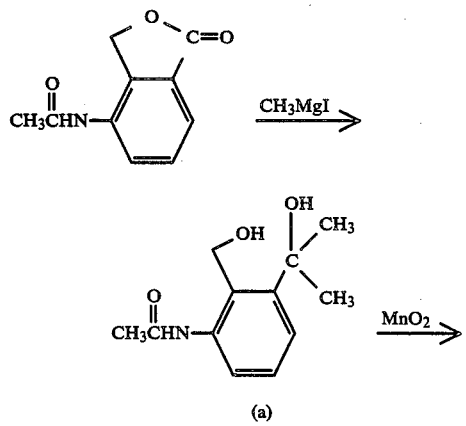

(a)

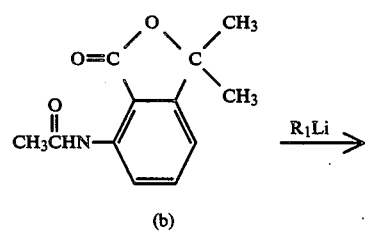

(b)

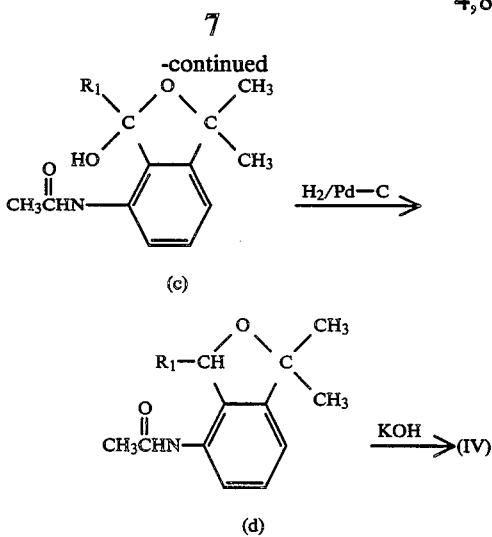

(c)

(d)

wherein $R_1$ is the same as that defined above.

That is, 4-acetaminophthalide is allowed to react with a methyl Grignard reagent such as methylmagnesium iodide (4-12 equivalents) in an ether solvent such as diethyl ether and tetrahydrofuran at a temperature from $-10°$ C. to room temperature, until diol (a) is obtained. The diol (a) is allowed to react with activated manganese dioxide (5-20 equivalents) in an ether solvent such as dioxane and tetrahydrofuran or a halogenated hydrocarbon solvent such as chloroform and dichloroethane under refluxing to obtain lactone (b). Then, the lactone (b) is allowed to react with methyllithium or ethyllithium (2-4 equivalents) in an ether solvent such as diethyl ether and tetrahydrofuran at a temperature from $-30°$ C. to room temperature until acetal (c) is obtained. The acetal (c) is allowed to react with hydrogen in an alcohol solvent such as methanol and ethanol at room temperature in the presence of catalytic amounts of palladium carbon and conc. hydrochloric acid until anilide (d) is obtained. The anilide (d) is then allowed to react with alkali metal hydroxide such as sodium hydroxide and potassium hydroxide (5-20 equivalents) in an ethylene glycol and water solvent under refluxing, until substituted 4-amino-2-oxaindan (IV) is obtained.

Substituted 4-amino-2-oxaindan having the formula (VI) may be obtained by, for example, optical resolution of substituted 4-amino-2-oxaindan (IV) with (1) optically active carboxylic acid or (2) an optically active column.

When the present compound is used as an active ingredient of fungicides, it may be used without adding any other components, but usually, it is formulated into emulsifiable concentrates, wettable powders, suspension formulations, granules, dusts, liquids and the like by mixing with a solid or liquid carrier, a surface active agent and other auxiliaries for formulation.

The content of the present compound as an active ingredient in these formulations is 0.1 to 99.9%, preferably 0.2 to 80% by weight.

The solid carriers include, for example, fine powders or granules of kaolin clay, attapulgite clay, bentonite, acid clay, pyrophyllite, talc, diatomaceous earth, calcite, corn starch powder, walnut shell powder, urea, ammonium sulfate, synthetic hydrated silicon dioxide and the like. The liquid carrier includes for example aromatic hydrocarbons such as xylene, methylnaphthalene and the like, alcohols such as isopropanol, ethylene glycol, cellosolve and the like, ketones such as acetone, cyclohexanone, isophorone and the like, vegetable oils such as soybean oil, cotton seed oil and the like, dimethyl sulfoxide, acetonitrile, water and the like.

The surface active agents used for emulsification, dispersion, wetting, etc. include, for example, anionic surface active agents such as salts of alkyl sulfate, alkyl (aryl) sulfonates, dialkyl-sulfosuccinates, salts of polyoxyethylene alkylaryl ether phosphoric acid esters, naphthalenesulfonic acid/formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliaries for formulation include, for example, lignosulfonates, alginates, polyvinyl alcohol, gum arabic, CMC (carboxymethyl cellulose), PAP (acid isopropyl phosphate), etc.

These formulations as such or diluted with, for example, water are applied to soil or directly to plants. In more detail, they are used in various forms, e.g., spraying or dusting on plants or spraying, dusting or granule-sprinkling onto soil surface or if necessary, subsequent further soil incorporation. Furthermore, when they are used as seed treating agents, seeds are covered therewith or dipped therein. These formulations may also be used in admixture with other fungicides, insecticides, acaricides, nematocides, herbicides, plant growth regulating agent, fertilizers, soil improvers and the like.

The present compounds are used as an active ingredient of fungicides to be used for paddy field, plowland, orchard, pasture, turf and the like.

When the present compound is used as an active ingredient of fungicide, its dosage is usually 0.5 to 100 g, preferably 1 to 50 g per are, although it depends on weather conditions, form of formulations, time, method and place of application, diseases to be controlled, crops to be treated, etc. When the emulsifiable concentrate, wettable powder, suspension formulation, liquid formulation, etc. are diluted with water for use, the concentration is 0.0001% to 1%, preferably 0.0005% to 0.5%. Granule and dust are used as they are without any dilution.

The present compound is able to be used as an active ingredient of fungicides for various kinds of applications, since the present compound is remarkably active against various plant diseases, particularly those by microorganisms belonging to Basidiomycetes.

The present invention will be explained in more detail by the following synthesis examples, reference examples, formulation examples and test examples.

Synthesis Example 1 [Synthesis of compound (2) by method (A)]

To a solution of 80 mg of 1,1,3-trimethyl-2-oxa-4-aminoindan and 50 mg of triethylamine in 5 ml of tetrahydrofuran was added dropwise with stirring below 5° C. of inner temperature under ice cooling, a solution of 89 mg of 5-chloro-1,3-dimethylpyrazole-4-carbonyl chloride in 2 ml of tetrahydrofuran, followed by stirring at room temperature overnight. The reaction mixture was extracted with water and chloroform. The organic layer was washed with water, dried and concentrated. The residue was purified by silica gel thin layer chromatography to obtain 119 mg of N-(1,1,3-trimethyl-2-oxa-4-indanyl)-5-chloro-1,3-dimethylpyrazole-4-carboxamide.

Synthesis Example 2 [Synthesis of compound (13) by method (A)]

To a solution of 70 mg of 1,1,3-trimethyl-2-oxa-4-aminoindan and 44 mg of triethylamine in 5 ml of tetrahydrofuran was added dropwise a solution of 83 mg of 2-(trifluoromethyl)benzoyl chloride in 2 ml of tetrahydrofuran under stirring at a temperature below 5° C. under ice cooling, followed by stirring at room temperature overnight. Then the reaction mixture was extracted with water and chloroform. The organic layer was washed with 5% hydrochloric acid and water, dried and concentrated. The residue was purified by silica gel thin layer chromatography to obtain 102 mg of N-(1,1,3-trimethyl-2-oxa-4-indanyl)-2-(trifluoromethyl)benzamide.

Synthesis Example 3 [Synthesis of compound (19) by method (A)]

A solution of 155 mg of 2-methylnicotinic acid and 335 mg of 1-(3-dimethylaminopropyl)-3-ethylcarbodiimide methiodide in 10 ml of methylene chloride was stirred at room temperature for 1 hour. To the solution was added 200 mg of 1,1,3-trimethyl-2-oxa-4-aminoindan and the reaction was made to proceed for 6 hours under refluxing. To the reaction mixture were added methylene chloride and water to extract an organic layer. The organic layer was concentrated and purified by silica gel thin layer chromatography to obtain 130 mg of N-(1,1,3-trimethyl-2-oxa-4-indanyl)-2-methylnicotinamide.

Synthesis Example 4 [Synthesis of compound (24) by method (A)]

To a solution of 100 mg of 1,1,3-trimethyl-2-oxa-4-aminoindan and 63 mg of triethylamine in 5 ml of tetrahydrofuran was added a solution of 130 mg of 2-methyl-4-trifluoromethylthiazole-5-carbonyl chloride in 2 ml of tetrahydrofuran under stirring at inner temperature of below 5° C. under ice cooling. After the dropwise addition was over, the reaction mixture was stirred overnight at room temperature, extracted with water and chloroform. The organic layer was washed with 5% hydrochloric acid and water, dried and concentrated. The residue was purified by silica gel thin layer chromatography to obtain 172 mg of N-(1,1,3-trimethyl-2-oxa-4-indanyl)-2-methyl-4-trifluoromethylthiazole-5-carboxamide.

Synthesis Example 5 [Synthesis of compound (26) by method (C)]

A solution of 193 mg of N-(1,1,3-trimethyl-2-oxa-4-indanyl)-2-chloroacetoacetamide and 49 mg of thioacetamide in 10 ml of tetrahydrofuran was allowed to react for 3 hours under refluxing.

To the reaction mixture was added 90 mg of anhydrous potassium carbonate and the mixture was allowed to react for 4 hours under refluxing. After the reaction was over, thereto were added chloroform and water to separate an organic layer. The organic layer was dried, concentrated and purified by silica gel thin layer chromatography to obtain 89 mg of N-(1,1,3-trimethyl-2-oxa-4-indanyl)-2,4-dimethylthiazole-5-carboxamide.

Some of representative compounds of the present invention which are able to be produced by these methods are shown in Table 1.

TABLE 1

Compound represented by the formula:

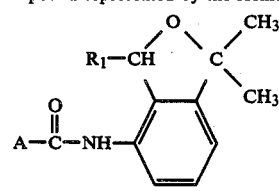

| Compound No. | A | $R_1$ | Melting point (°C.) |
|---|---|---|---|
| (1) | 1,5-dimethylpyrazol-4-yl | $CH_3$ | 95.8 |
| (2) | 3-chloro-1,5-dimethylpyrazol-4-yl | $CH_3$ | 145.0 |
| (3) | 3-bromo-1,5-dimethylpyrazol-4-yl | $CH_3$ | 162.1 |
| (4) | 3-fluoro-1,5-dimethylpyrazol-4-yl | $CH_3$ | 101.3 |
| (5) | 1,5-dimethylpyrazol-4-yl (H) | $CH_3$ | 142.1 |
| (6) | 1-methyl-3-methyl-5-trifluoromethylpyrazol-4-yl | $CH_3$ | — |
| (7) | 3-chloro-1-methyl-5-trifluoromethylpyrazol-4-yl | $CH_3$ | 156.4 |

TABLE 1-continued

Compound represented by the formula:

(structure: $R_1$-CH-O-C(CH$_3$)$_2$ fused to benzene ring with A-C(=O)-NH- substituent)

| Compound No. | A | $R_1$ | Melting point (°C.) |
|---|---|---|---|
| (8) | 3-CF$_3$-1-methylpyrazol-4-yl (with H at 5-position) | CH$_3$ | 160.5 |
| (9) | 3-C$_2$H$_5$-5-Cl-1-methylpyrazol-4-yl | CH$_3$ | 99.2 |
| (10) | 3,5-diCH$_3$-1-methylpyrazol-4-yl | C$_2$H$_5$ | 139.9 |
| (11) | 3-CH$_3$-5-Cl-1-methylpyrazol-4-yl | C$_2$H$_5$ | — |
| (12) | 2-CH$_3$-phenyl | CH$_3$ | 141.8 |
| (13) | 2-CF$_3$-phenyl | CH$_3$ | 188.6 |
| (14) | 2-Cl-phenyl | CH$_3$ | 129.9 |
| (15) | 2-Br-phenyl | CH$_3$ | — |
| (16) | 2-I-phenyl | CH$_3$ | 171.4 |
| (17) | 2-NO$_2$-phenyl | CH$_3$ | 189.6 |
| (18) | 2-F-6-Cl-phenyl | CH$_3$ | 153.1 |
| (19) | 2-CH$_3$-pyridin-3-yl | CH$_3$ | 161.1 |
| (20) | 2-CF$_3$-pyridin-3-yl | CH$_3$ | 187.4 |
| (21) | 2-Cl-pyridin-3-yl | CH$_3$ | 156.5 |
| (22) | 2-NO$_2$-pyridin-3-yl | CH$_3$ | 161.4 |
| (23) | 2-Cl-4-CF$_3$-thiazol-5-yl | CH$_3$ | 149.1 |
| (24) | 2-CH$_3$-4-CF$_3$-thiazol-5-yl | CH$_3$ | 167.6 |
| (25) | 2-Cl-4-CH$_3$-thiazol-5-yl | CH$_3$ | 93.0 |
| (26) | 2-CH$_3$-4-CH$_3$-thiazol-5-yl | CH$_3$ | 134.8 |

TABLE 1-continued

Compound represented by the formula:

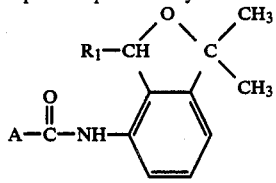

| Compound No. | A | R₁ | Melting point (°C.) |
|---|---|---|---|
| (27) | ![structure with N, CH₃, H₂N, S] | CH₃ | 189.0 |
| (28) | ![structure with N, C₂H₅, CH₃, S] | CH₃ | |

Synthesis Example 6 [Synthesis of compound (29) by method (B)]

To a solution of 160 mg of (3S)-1,1,3-trimethyl-2-oxa-4-aminoindan and 79 mg of pyridine in 10 ml of tetrahydrofuran was added dropwise a solution of 178 mg of 5-chloro-1,3-dimethylpyrazole-4-carbonyl chloride in 4 ml of tetrahydrofuran with stirring at a temperature of below 5° C. of inner temperature under ice cooling, followed by stirring at room temperature overnight. Extraction was made with water and chloroform. The organic layer was washed with 1% hydrochloric acid, dried and concentrated. The residue was purified by silica gel thin layer chromatography to obtain 262 mg of N-[(3S)-1,1,3-trimethyl-2-oxa-4-indanyl]-5-chloro-1,3-dimethylpyrazole-4-carboxamide (yield 87%).

Synthesis Example 7 [Synthesis of compound (29) by method (D)]

N-(1,1,3-trimethyl-2-oxa-4-indanyl)-5-chloro-1,3-dimethylpyrazole-4-carboxamide was separated into enantiomers by a "Sumipack OA"-4100 optically active column [eluent; hexane: 1,2-dichloroethane: ethanol=500:150:1.5]. The desired N-[(3S)-1,1,3-trimethyl-2-oxa-4-indanyl]-5-chloro-1,3-dimethylpyrazole-4-carboxamide was eluted as a fore-peak (yield 38%).

The present compound (29) obtained by the above synthesis example showed the following properties:
m.p. 169.1° C.
$[\alpha]_D^{24.0} = -74.3°$ (CHCl₃, c 1.0).

Preparation of substituted 4-amino-2-oxaindan represented by the formula (IV) will be explained below.

Reference Example 1

Synthesis of α,α-dimethyl-2-hydroxymethyl-3-acetaminobenzyl alcohol

To a mixture of 9.5 g of metallic magnesium and 60 ml of diethyl ether was slowly added with stirring a solution of 56 g of methyl iodide in 120 ml of diethyl ether. The mixed solution was heated for 15 minutes under refluxing and cooled. The solution of methylmagnesium iodide thus prepared above in ether was slowly added with stirring at inner temperature of below 10° C. to a solution of 7.5 g of 4-acetaminophthalide in 120 ml of tetrahydrofuran, followed by stirring at room temperature overnight. After the reaction was over, the reaction mixture was poured into aqueous ammonium chloride solution (saturated) under ice cooling and extracted twice with 400 ml of ethyl acetate. The combined extracts were dried and concentrated to obtain an oily substance. The oily substance was purified by silica gel column chromatography to obtain 7.2 g of α,α-dimethyl-2-hydroxymethyl-3-acetaminobenzyl alcohol in the white crystal form. m.p. 137.9° C.

'H-NHR (CDCl₃) δppm: 1.6 (6H, s), 2.1 (3H, s), 3.7 (2H, br s), 5.0 (2H, s), 7.2–7.8 (3H, m), 8.7 (1H, br s).

Reference Example 2

Synthesis of 3,3-dimethyl-7-acetaminophthalide

To a solution of 7.2 g of α,α-dimethyl-2-hydroxymethyl-3-acetaminobenzyl alcohol in 300 ml of chloroform was added 28 g of activated manganese dioxide and the mixture was allowed to react for 6 hours under refluxing. After the reaction was over, the reaction mixture was left to stand for cooling and filtered on a glass filter having a bed of celite. The residue was washed with 100 ml of chloroform. The filtrate and the washed solution were combined and concentrated to obtain an oily substance. The oily substance was purified by silica gel column chromatography to obtain 4.4 g of 3,3-dimethyl-7-acetaminophthalide in the white crystal form. m.p. 124.1° C.

'H-NMR δppm: 1.6 (6H, s), 2.2 (3H, s), 7.0 (1H, d, J=8.0 Hz), 7.6 (1H, t, J=8.0 Hz), 8.5 (1H, d, J=8.0 Hz), 9.7 (1H, br s).

Reference Example 3

Synthesis of 1,1,3-trimethyl-3-hydroxy-2-oxa-4-acetaminoindan

To a solution of 4.4 g of 3,3-dimethyl-7-acetaminophthalide in 80 ml of tetrahydrofuran was slowly added dropwise 43 ml of a solution of methyllithium in ether (1.4M) at −20° C., followed by stirring at the same temperature for 20 minutes. After the reaction was over, the reaction mixture was poured into aqueous ammonium chloride solution (saturated) under ice cooling and extracted twice with 200 ml of ethyl acetate. The combined extracts were dried and concentrated to obtain 4.7 g of 1,1,3-trimethyl-3-hydroxy-2-oxa-4-acetaminoindan as an oily substance.

'H-NMR δppm: 1.5 (6H, s), 1.7 (3H, s), 2.1 (3H, s), 4.7 (1H, s), 6.85 (1H, d, J=8.0 Hz), 7.3 (1H, t, J=8.0 Hz), 7.9 (1H, d, J=8.0 Hz), 8.0 (1H, s).

Reference Example 4

Synthesis of 1,1,3-trimethyl-2-oxa-4-acetaminoindan

To a solution of 4.7 g of 1,1,3-trimethyl-3-hydroxy-2-oxa-4-acetaminoindan in 120 ml of ethanol were added catalytic amounts of conc. hydrochloric acid and 10% palladium carbon, and vigorously stirred for 6 hours at room temperature under a hydrogen atmosphere. After the reaction was over, the reaction mixture was filtered on a glass filter having a bed of celite and the residue was washed with 60 ml of ethanol. The filtrate and the washed solution were combined and concentrated to obtain 4.3 g of 1,1,3-trimethyl-2-oxa-4-acetaminoindan in the oily substance form.

¹H-NMR δppm: 1.4 (3H, s), 1.4 (3H, d, J=6.0 Hz), 1.5 (3H, s), 2.1 (3H, s), 5.4 (1H, q, J=6.0 Hz), 6.8–7.4 (3H, m), 8.1 (1H, s).

Synthesis Example 8

Synthesis of 1,1,3-trimethyl-2-oxa-4-aminoindan

To a solution of 4.3 g of 1,1,3-trimethyl-2-oxa-4-acetaminoindan in 60 ml of ethylene glycol and 30 ml of water was added 11 g of potassium hydroxide and the mixture was heated under refluxing for 8 hours under a nitrogen atmosphere. After the reaction was over, the reaction mixture was left to stand for cooling, diluted with 60 ml of water and extracted with 60 ml of chloroform four times. The combined extracts were washed with water three times, dried and concentrated. The oily substance obtained was purified by silica gel thin layer chromatography to obtain 2.0 g of 1,1,3-trimethyl-2-oxa-4-aminoindan in the white crystal form. m.p. 75.5° C.

¹H-NMR δppm: 1.4 (3H, s), 1.5 (3H, d, J=6.0 Hz), 1.5 (3H, s), 3.6 (2H, br s), 5.25 (1H, q, J=6.0 Hz), 6.2–6.7 (2H, m), 7.1 (1H, dd, each J=6.0 Hz).

Synthesis Example 9

1,1-Dimethyl-3-ethyl-2-oxa-4-aminoindan was obtained by the similar method to Synthesis Example 8.

¹H-NMR δppm: 1.0 (3H, t, J=6.0 Hz), 1.45 (3H, s), 1.55 (3H, s), 1.4–2.1 (2H, m), 3.5 (2H, br s), 5.15 (1H, dd, J=6.0 Hz, 4.0 Hz), 6.45 (2H, br d), 7.0 (1H, dd, J=8.0 Hz, J=6.0 Hz).

The following are formulation examples where the present compounds used are indicated by the numbers given in Table 1 and Synthesis Examples and parts are by weight.

Formulation Example 1

Fifty parts of each of the present compounds (1)–(29), 3 parts of calcium lignosulfonate, 2 parts of sodium lauryl sulfate and 45 parts of synthetic hydrated silicon dioxide are thoroughly pulverized and mixed to obtain a wettable powder containing an active ingredient concentration of 50%.

Formulation Example 2

Ten parts of each of the present compounds (1)–(29), 14 parts of polyoxyethylenestyrylphenyl ether, 6 parts of calcium dodecylbenzenesulfonate and 70 parts of xylene are thoroughly mixed to obtain an emulsifiable concentrate containing an active ingredient concentration of 10%.

Formulation Example 3

Two parts of each of the present compounds (1)–(29), 1 part of synthetic hydrated silicon dioxide, 2 parts of calcium lignosulfonate, 30 parts of bentonite, and 65 parts of kaolin clay are thoroughly pulverized and mixed, well kneaded with water, then granulated and dried to obtain a granule containing an active ingredient concentration of 2%.

Formulation Example 4

Twentyfive parts of each of the present compounds (1)–(29), 3 parts of polyoxyethylenesorbitan monooleate, 3 parts of CMC and 69 parts of water are mixed and wet-pulverized to particle size of not more than 5 microns to obtain a suspension formulation containing an active ingredient concentration of 25%.

Formulation Example 5

Two parts of each of the present compounds (1)–(29), 88 parts of kaolin clay and 10 parts of talc are thoroughly pulverized and mixed to obtain a dust containing an active ingredient concentration of 2%.

Formulation Example 6

Ten parts of each of the present compounds (1)–(29), 1 part of polyoxyethylenestyrylphenyl ether and 89 parts of water are mixed to obtain a liquid containing an active ingredient concentration of 10%.

The effect of the present compounds as an active ingredient of fungicides will be shown by the following test examples. The present compounds used are indicated by the compound number given in Table 1 and Synthesis Examples and the compounds used for comparison are indicated by the compounds given in Table 2.

TABLE 2

| Compounds | Chemical formula | Note |
|---|---|---|
| A | [structure: 2-methylphenyl-C(=O)NH-3-isopropoxyphenyl] | Commercially available fungicide (mepronil) |
| B | [structure: (CH₃)₂N-N=C(CH₃)-C(CH₃)=C(C(=O)NH-3-isopropoxyphenyl)] | Compound mentioned in Japanese Kokai 60-34949 |
| C | [structure: 2-methyl-4-methylthiazole with C(=O)-NH-phenyl] | Compound mentioned in Phytopathology 60; 1164–1169 (1970) |

TABLE 2-continued

| Compounds | Chemical formula | Note |
|---|---|---|
| D | (pyridine with CH$_3$ at 3-position, C(=O)-NH- linker to phenyl with OC$_3$H$_7$(i)) | Compound mentioned in Japanese Kokai 58-96069 |

The controlling effect is determined by observing with the naked eye the condition of disease of test plants on examination, namely, the degree of fungus colony and infected area of leaf and stem and grading the condition of diseases into the following six indices 0, 1, 2, 3, 4 and 5:

5 ... No infected area and fungus colony are noticed.
4 ... Infected area and fungus colony are noticed in about 10% of leaf and stem.
3 ... Infected area and fungus colony are noticed in about 30% of leaf and stem.
2 ... Infected area and fungus colony are noticed in about 50% of leaf and stem.
1 ... Infected area and fungus colony are noticed in about 70% of leaf and stem.
0 ... Infected area and fungus colony are noticed in more than about 70% and no difference is noticed from the condition of disease when no compound is used.

The above grading is applied to all of the following test examples.

Test Example 1

Test for preventive controlling effect on sheath blight (*Rhizoctonia solani*) of rice Sandy loam was filled in a plastic pot and rice (var.: Kinki No. 33) was sowed and cultivated in a greenhouse for 20 days to grow to seedlings in the 4–5 leaf stages. The test compounds were formulated into emulsifiable concentrates in accordance with the Formulation Example 2 and they were diluted with water to a given concentration. These were foliar-sprayed onto the seedlings to allow them to thoroughly deposit on the leaf surface. After 4 hours from the spraying, the seedlings were inoculated with agar piece containing *Rhizoctonia solani*. After inoculation, the seedlings were grown at 28° C. for 4 days under highly humid condition and the controlling effects were observed. The results are shown in Table 3.

TABLE 3

| Test compounds | Concentration of active ingredient (ppm) | Controlling effect |
|---|---|---|
| (1) | 50 | 5 |
|  | 25 | 5 |
| (2) | 50 | 5 |
|  | 25 | 5 |
| (3) | 50 | 5 |
|  | 25 | 5 |
| (4) | 50 | 5 |
|  | 25 | 5 |
| (5) | 50 | 5 |
|  | 25 | 5 |
| (7) | 50 | 5 |
|  | 25 | 5 |
| (8) | 50 | 5 |
|  | 25 | 5 |
| (9) | 50 | 5 |
|  | 25 | 5 |
| (10) | 50 | 5 |
|  | 25 | 5 |

TABLE 3-continued

| Test compounds | Concentration of active ingredient (ppm) | Controlling effect |
|---|---|---|
| (12) | 50 | 5 |
|  | 25 | 5 |
| (13) | 50 | 5 |
|  | 25 | 5 |
| (14) | 50 | 5 |
|  | 25 | 5 |
| (16) | 50 | 5 |
|  | 25 | 5 |
| (17) | 50 | 5 |
|  | 25 | 5 |
| (18) | 50 | 5 |
|  | 25 | 5 |
| (19) | 50 | 5 |
|  | 25 | 5 |
| (20) | 50 | 5 |
|  | 25 | 5 |
| (21) | 50 | 5 |
|  | 25 | 5 |
| (22) | 50 | 5 |
|  | 25 | 5 |
| (23) | 50 | 5 |
| (24) | 50 | 5 |
| (25) | 50 | 5 |
| (26) | 50 | 5 |
| (27) | 50 | 5 |
| (29) | 50 | 5 |
|  | 25 | 5 |
|  | 12.5 | 5 |
| A | 50 | 3 |
|  | 25 | 0 |
| B | 50 | 3 |
|  | 25 | 0 |
| C | 50 | 2 |
|  | 25 | 0 |
| D | 50 | 2 |
|  | 25 | 0 |

Test Example 2

Test for systemic controlling effect on sheath blight (*Rhizoctonia solani*) of rice Sandy loam was filled in a 130 ml plastic pot and rice (var.: Kinki No. 33) was sowed and cultivated in a greenhouse for 3 weeks to grow to seedlings in the 4–5 leaf stages. The test compounds formulated into wettable powders in accordance with Formulation Example 1 and they were diluted with water and drenched in a given amount to the soil. After drench, the seedlings were grown in a greenhouse for 7 days and inoculated with agar piece containing *Rhizoctonia solani*. After inoculation, the seedlings were grown at 28° C. for 4 days under a highly humid condition and the controlling effect was observed. The results are shown in Table 4.

TABLE 4

| Test compounds | Dosage of active ingredient (g/10a) | Controlling effect |
|---|---|---|
| (1) | 200 | 5 |
|  | 100 | 5 |
| (2) | 200 | 5 |

TABLE 4-continued

| Test compounds | Dosage of active ingredient (g/10a) | Controlling effect |
| --- | --- | --- |
| (3) | 100 | 5 |
|  | 200 | 5 |
| (4) | 100 | 5 |
|  | 200 | 5 |
| (5) | 100 | 5 |
|  | 200 | 5 |
| (7) | 100 | 5 |
|  | 200 | 5 |
| (8) | 100 | 5 |
|  | 200 | 5 |
| (9) | 100 | 5 |
|  | 200 | 5 |
| (10) | 100 | 5 |
|  | 200 | 5 |
| (12) | 100 | 5 |
|  | 200 | 5 |
| (13) | 200 | 5 |
| (14) | 200 | 5 |
| (16) | 200 | 5 |
| (17) | 200 | 5 |
| (18) | 200 | 5 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (29) | 200 | 5 |
|  | 100 | 5 |
|  | 50 | 5 |
| A | 200 | 3 |
|  | 100 | 0 |
| B | 200 | 3 |
|  | 100 | 0 |
| C | 200 | 2 |
|  | 100 | 0 |
| D | 200 | 2 |
|  | 100 | 0 |

Test Example 3

Test for controlling effect on southern blight (*Corticium rolfsii*) of kidney bean Sandy loam well mixed with *Corticium rolfsii* which was previously cultured in bran medium was filled in a 250 ml plastic pot and kidney bean (var.: Taishokintoki) was sowed. The test compounds were formulated into wettable powders in accordance with Formulation Example 1 and diluted with water. A given amount of the test compound was drenched into the soil. After the drench, cultivation was made for 3 weeks in a greenhouse and controlling effect was examined by observing the degree of disease of the stem in the vicinity of the soil surface. The results are shown in Table 5.

TABLE 5

| Test compounds | Dosage of active ingredient (g/10a) | Controlling effect |
| --- | --- | --- |
| (1) | 200 | 5 |
| (2) | 200 | 5 |
| (3) | 200 | 5 |
| (4) | 200 | 5 |
| (5) | 200 | 5 |
| (7) | 200 | 5 |
| (8) | 200 | 5 |
| (9) | 200 | 5 |
| (10) | 200 | 5 |
| (12) | 200 | 5 |
| (13) | 200 | 5 |
| (14) | 200 | 5 |
| (16) | 200 | 5 |

TABLE 5-continued

| Test compounds | Dosage of active ingredient (g/10a) | Controlling effect |
| --- | --- | --- |
| (17) | 200 | 4 |
| (18) | 200 | 4 |
| (19) | 200 | 5 |
| (20) | 200 | 5 |
| (21) | 200 | 5 |
| (22) | 200 | 5 |
| (23) | 200 | 5 |
| (24) | 200 | 5 |
| (25) | 200 | 5 |
| (26) | 200 | 5 |
| (27) | 200 | 5 |
| (29) | 200 | 5 |
|  | 100 | 5 |
| A | 200 | 0 |
| B | 200 | 0 |
| C | 200 | 0 |
| D | 200 | 0 |

Test Example 4

Test for curative controlling effect on brown rust (*Puccinia recondita*) of wheat Sandy loam was filled in a plastic pot and wheat (var.: Norin No. 73) was sowed and grown in a greenhouse for 10 days to seedlings of the 2–3 leaf stages, which were inoculated with spores of *Puccinia recondita*. After inoculation, the seedlings were grown at 23° C. for one day under a highly humid condition and onto these seedlings was foliar-sprayed the test compound formulated into emulsifiable concentrate in accordance with Formulation Example 2 and diluted with water to a given concentration, so that the compound was thoroughly deposited on the leaf surface. After spraying, the seedlings were cultivated at 23° C. for 7 days under illumination and the controlling effect was observed. The results are shown in Table 6.

TABLE 6

| Test compounds | Concentration of active ingredient (ppm) | Controlling effect |
| --- | --- | --- |
| (1) | 500 | 5 |
| (2) | 500 | 5 |
| (3) | 500 | 5 |
| (4) | 500 | 5 |
| (5) | 500 | 5 |
| (7) | 500 | 5 |
| (8) | 500 | 5 |
| (9) | 500 | 5 |
| (10) | 500 | 5 |
| (12) | 500 | 5 |
| (13) | 500 | 5 |
| (14) | 500 | 5 |
| (16) | 500 | 5 |
| (17) | 500 | 5 |
| (18) | 500 | 5 |
| (19) | 500 | 5 |
| (20) | 500 | 5 |
| (21) | 500 | 5 |
| (22) | 500 | 5 |
| (23) | 500 | 5 |
| (24) | 500 | 5 |
| (25) | 500 | 5 |
| (26) | 500 | 5 |
| (27) | 500 | 5 |
| (29) | 500 | 5 |

We claim:

1. A substituted carboxylic acid derivative having the formula:

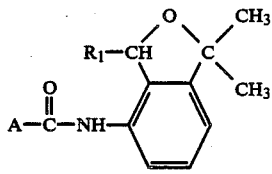

wherein $R_1$ stands for a methyl or ethyl group, A stands for

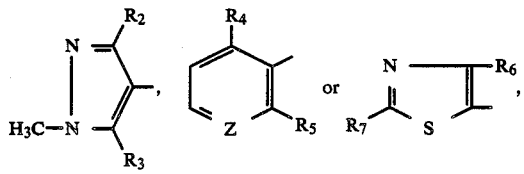

$R_2$ stands for a methyl, ethyl or trifluoromethyl group, $R_3$ stands for a methyl group or a halogen or hydrogen atom, $R_4$ stands for a fluorine or hydrogen atom, $R_5$ stands for a methyl, nitro or trifluoromethyl group or a halogen atom, Z stands for an N atom, $R_6$ stands for a methyl, ethyl or trifluoromethyl group and $R_7$ stands for an amino or methyl group or a chlorine atom.

2. A substituted carboxylic acid derivative having the formula:

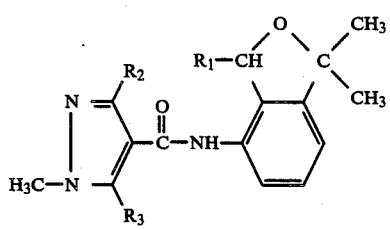

wherein $R_1$ stands for a methyl or ethyl group, $R_2$ stands for a methyl, ethyl or trifluoromethyl group and $R_3$ stands for a methyl group or a halogen or hydrogen atom.

3. A substituted carboxylic acid derivative having the formula:

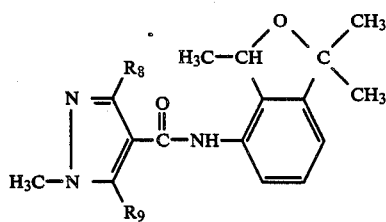

wherein $R_8$ stands for a methyl or trifluoromethyl group and $R_9$ stands for a halogen atom.

4.

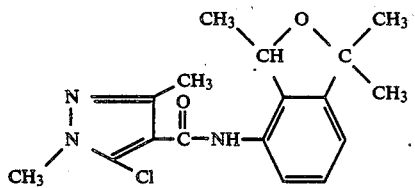

5.

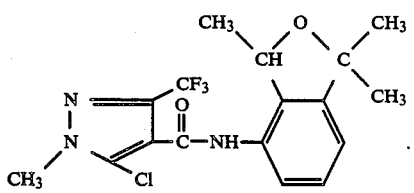

6.

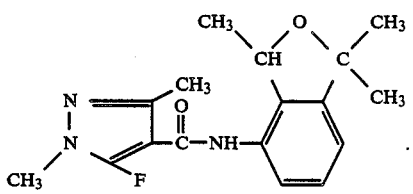

7. A substituted carboxylic acid derivative having the formula:

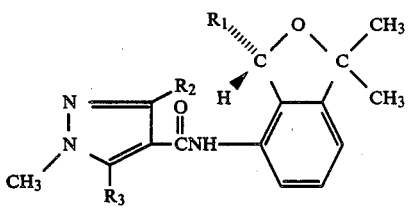

wherein $R_1$ stands for a methyl or ethyl group, $R_2$ stands for a methyl, ethyl or trifluoromethyl group and $R_3$ stands for a methyl group or a halogen or hydrogen atom.

8. An agricultural or horticultural fungicide which contains, as an active ingredient, a substituted carboxylic acid derivative having the formula:

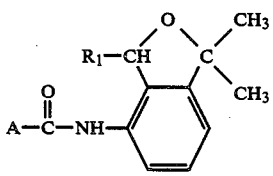

wherein $R_1$ stands for a methyl or ethyl group, A stands for

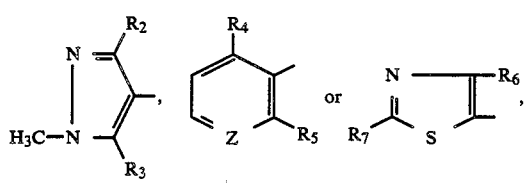 or 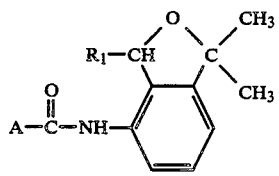, $R_2$ stands for a methyl, ethyl or trifluoromethyl group, $R_3$ stands for a methyl group or a halogen or hydrogen atom, $R_4$ stands for a fluorine or hydrogen atom, $R_5$ stands for a methyl, nitro or trifluoromethyl group or a halogen atom, Z stands for an N atom, $R_6$ stands for a methyl, ethyl or trifluoromethyl group and $R_7$ stands for an amino or methyl group or a chlorine atom, with an inert carrier.

9. An agricultural or horticultural fungicide which contains, as an active ingredient, a substituted carboxylic acid derivative having the formula:

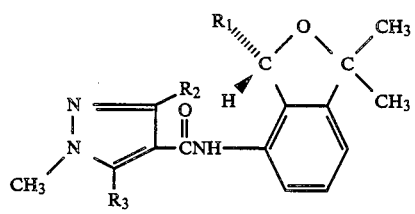

wherein $R_1$ stands for a methyl or ethyl group, $R_2$ stands for a methyl, ethyl or trifluoromethyl group and $R_3$ stands for a methyl group or a halogen or hydrogen atom, with an inert carrier.

10. A method for controlling fungi which comprises applying to fungi a fungicidally effective amount of a substituted carboxylic acid derivative having the formula:

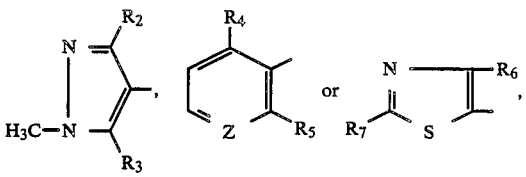

wherein $R_1$ stands for a methyl or ethyl group, A stands for

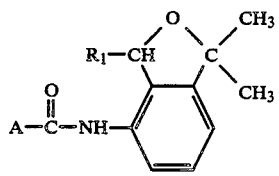

$R_2$ stands for a methyl, ethyl or trifluoromethyl group, $R_3$ stands for a methyl group or a halogen or hydrogen atom, $R_4$ stands for a fluorine or hydrogen atom, $R_5$ stands for a methyl, nitro or trifluoromethyl group or a halogen atom, Z stands for an N atom, $R_6$ stands for a methyl, ethyl or trifluoromethyl group and $R_7$ stands for an amino or methyl group or a chlorine atom, to fungi.

11. A method for controlling fungi which comprises applying to fungi a fungicidally effective amount of a substituted carboxylic acid derivative having the formula:

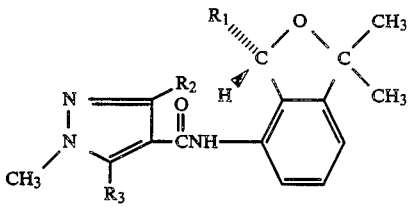

wherein $R_1$ stands for a methyl or ethyl group, $R_2$ stands for a methyl, ethyl or trifluoromethyl group and $R_3$ stands for a methyl group or a halogen or hydrogen atom, to fungi.

12. The method according to claim 10 or 11 wherein the fungi are a plant pathogenic fungi.

* * * * *